(12) United States Patent
Milo et al.

(10) Patent No.: US 6,511,458 B2
(45) Date of Patent: *Jan. 28, 2003

(54) VASCULAR RE-ENTRY CATHETER

(75) Inventors: Charles F. Milo, Union City, CA (US); Matthew R. Selmon, Woodside, CA (US); Richard E. Hill, Berkeley, CA (US); Fred H. Co, Santa Clara, CA (US); Ronald G. French, Palo Alto, CA (US)

(73) Assignee: LuMend, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/765,777

(22) Filed: Jan. 19, 2001

(65) Prior Publication Data

US 2001/0012924 A1 Aug. 9, 2001

Related U.S. Application Data

(60) Continuation of application No. 09/440,308, filed on Nov. 17, 1999, now Pat. No. 6,235,000, which is a division of application No. 09/006,563, filed on Jan. 13, 1998, now Pat. No. 6,231,546.

(51) Int. Cl.[7] .......................... A61M 5/178; A61M 5/32; A61B 5/00
(52) U.S. Cl. ................... 604/164.13; 604/272; 600/585
(58) Field of Search ................................ 604/158–161, 604/164.01, 164.07, 164.09, 164.11, 164.13, 165.01, 165.02, 165.04, 170.03, 264, 272, 500, 523, 508

(56) References Cited

U.S. PATENT DOCUMENTS

| | | | |
|---|---|---|---|
| 1,747,407 A | 2/1930 | Wappler | |
| 4,405,314 A | 9/1983 | Cope | ............................ 604/51 |
| 4,552,554 A | 11/1985 | Gould et al. | ................... 604/51 |
| 4,648,402 A | 3/1987 | Santos | ......................... 128/345 |
| 4,774,949 A | 10/1988 | Fogarty | .................... 128/348.1 |
| 4,947,864 A | 8/1990 | Shockey et al. | ............... 358/98 |
| 5,001,556 A | 3/1991 | Nakamura et al. | ............. 358/98 |
| 5,019,040 A | 5/1991 | Itaoka et al. | .................. 604/95 |
| 5,061,245 A | 10/1991 | Waldvogel | .................. 604/170 |

(List continued on next page.)

FOREIGN PATENT DOCUMENTS

| | | | |
|---|---|---|---|
| DE | 2945237 | 5/1981 | ........... A61B/17/22 |
| DE | 4429117 | 2/1996 | ........... A61M/29/00 |
| EP | 0 377 269 | 7/1990 | ........... A61M/25/01 |
| FR | 1585065 | 1/1970 | |

(List continued on next page.)

OTHER PUBLICATIONS

Jean Paul Melchior, et al., "Perceutaneous Transluminal Coronary Angioplasty for Chronic Total Coronary Artial Occlusion", American Journal of Cardiology 1987; 59–535–538.

(List continued on next page.)

*Primary Examiner*—Sharon Kennedy
(74) *Attorney, Agent, or Firm*—Shemwell Gregory & Courtney LLP

(57) ABSTRACT

Total occlusions are crossed by passing a guidewire or other penetrating wire from a point proximal to the occlusion into a subintimal space between the intimal layer and adventitial layer of the blood vessel wall. The wire is advanced to a point distal to the occlusion and thereafter deflected back into the blood vessel lumen, typically using a deflecting catheter which is advanced over the guidewire after it has been positioned within the subintimal space. After the guidewire is returned to the blood vessel lumen, the deflecting catheter may be withdrawn and the guidewire is available for introduction of other interventional and diagnostic catheters.

12 Claims, 11 Drawing Sheets

U.S. PATENT DOCUMENTS

| | | | |
|---|---|---|---|
| 5,095,911 A | 3/1992 | Pomeranz | 128/662.06 |
| 5,099,850 A | 3/1992 | Matsui et al. | 128/662.06 |
| 5,109,830 A | 5/1992 | Cho | 128/4 |
| 5,114,414 A | 5/1992 | Buchbinder | 604/95 |
| 5,127,917 A | 7/1992 | Niederhauser et al. | 606/191 |
| 5,183,470 A | 2/1993 | Wettmann | 604/281 |
| 5,190,528 A | 3/1993 | Fonger et al. | 604/171 |
| 5,279,565 A | 1/1994 | Klein et al. | 604/105 |
| 5,287,861 A | 2/1994 | Wilk | 128/898 |
| 5,321,501 A | 6/1994 | Swanson et al. | 356/345 |
| 5,350,377 A | 9/1994 | Winston et al. | 606/15 |
| 5,389,096 A | 2/1995 | Aita et al. | 606/15 |
| 5,409,019 A | 4/1995 | Wilk | 128/898 |
| 5,409,453 A | 4/1995 | Lundquist et al. | 604/22 |
| 5,413,581 A | 5/1995 | Goy | 606/194 |
| 5,429,144 A | 7/1995 | Wilk | 128/898 |
| 5,443,497 A | 8/1995 | Venbrux | 623/1 |
| 5,452,733 A | 9/1995 | Sterman et al. | 128/898 |
| 5,456,694 A | 10/1995 | Marin et al. | 606/198 |
| 5,456,714 A | 10/1995 | Owen | 623/1 |
| 5,464,395 A | 11/1995 | Faxon et al. | 604/96 |
| 5,486,170 A | 1/1996 | Winston et al. | 606/16 |
| 5,573,531 A | 11/1996 | Gregory | 606/14 |
| 5,607,435 A | 3/1997 | Sachdeva et al. | 606/139 |
| 5,628,761 A | 5/1997 | Rizik | 606/170 |
| 5,695,457 A | 12/1997 | St. Goar et al. | 604/4 |
| 5,707,389 A | 1/1998 | Louw et al. | 606/200 |
| 5,741,270 A | 4/1998 | Hansen et al. | 606/108 |
| 5,830,222 A | 11/1998 | Mokower | 606/159 |
| 5,910,133 A | 6/1999 | Gould | 604/164 |
| 5,928,138 A * | 7/1999 | Knight et al. | 600/201 |
| 5,935,108 A | 8/1999 | Katoh et al. | 604/164 |
| 5,938,671 A | 8/1999 | Katoh et al. | 606/159 |
| 6,015,423 A | 1/2000 | Andrese | 606/198 |
| 6,036,713 A * | 3/2000 | Kieturakis | 606/190 |
| 6,068,638 A | 5/2000 | Makower | 606/159 |
| 6,071,292 A | 6/2000 | Makower et al. | 606/158 |
| 6,081,738 A * | 6/2000 | Hinohara et al. | 600/407 |
| 6,126,649 A | 10/2000 | Van Tassel et al. | 604/528 |
| 6,159,225 A | 12/2000 | Makower | 606/155 |
| 6,168,610 B1 * | 1/2001 | Marin et al. | 606/198 |
| 6,190,353 B1 | 2/2001 | Makower et al. | 604/95 |
| 6,231,587 B1 | 5/2001 | Makower | 606/198 |
| 6,283,951 B1 | 9/2001 | Flaherty et al. | 604/529 |
| 6,283,983 B1 | 9/2001 | Makower | 606/198 |
| 6,287,317 B1 * | 9/2001 | Makower et al. | 606/153 |
| 6,302,875 B1 * | 10/2001 | Makower et al. | 604/528 |
| 6,330,884 B1 | 12/2001 | Kim | 128/898 |
| 6,375,615 B1 | 4/2002 | Flaherty et al. | 600/439 |
| 2001/0047165 A1 | 11/2001 | Makower et al. | 604/528 |
| 2002/0002349 A1 | 1/2002 | Flaherty et al. | 604/164.11 |

FOREIGN PATENT DOCUMENTS

| | | | | |
|---|---|---|---|---|
| WO | WO97/13463 | 4/1797 | | A61B/17/00 |
| WO | WO97/13471 | 4/1797 | | A61B/19/00 |
| WO | WO 97/27897 | 8/1977 | | A61M/29/00 |
| WO | WO 83/03188 | 9/1983 | | A61B/01/06 |
| WO | WO 91/19528 | 12/1991 | | |
| WO | WO 92/08510 | 5/1992 | | A61M/25/00 |
| WO | WO 93/18818 | 9/1993 | | A61M/37/00 |
| WO | WO 95/02430 | 1/1995 | | |
| WO | WO 95/19143 | 7/1995 | | A61B/17/22 |
| WO | WO 96/01590 | 1/1996 | | |
| WO | WO 96/04035 | 2/1996 | | |
| WO | WO 97/13463 | 4/1997 | | A61B/17/00 |
| WO | WO 97/13471 | 4/1997 | | A61B/19/00 |
| WO | WO 97/26936 | 7/1997 | | |
| WO | WO97/27893 | 8/1997 | | A61M/19/00 |
| WO | WO 97/27893 | 8/1997 | | A61M/19/00 |
| WO | WO97/27897 | 8/1997 | | A61M/29/00 |
| WO | WO97/27898 | 8/1997 | | A61M/29/00 |
| WO | WO 97/27898 | 8/1997 | | A61M/29/00 |
| WO | WO 97/37581 | 10/1997 | | |
| WO | WO 97/44083 | 11/1997 | | |
| WO | WO 98/08456 | 3/1998 | | A61B/19/00 |
| WO | WO98/08456 | 3/1998 | | A61B/19/00 |
| WO | WO 98/16161 | 4/1998 | | A61B/17/36 |
| WO | WO 98/46115 | 10/1998 | | |
| WO | WO 98/466119 | 10/1998 | | A61B/1/00 |
| WO | WO 99/21490 | * 5/1999 | | |
| WO | WO 99/25273 | 5/1999 | | A61F/2/06 |
| WO | WO 99/48545 | 9/1999 | | A61M/5/00 |
| WO | WO 99/49793 | 10/1999 | | A61B/17/22 |
| WO | WO 99/49910 | 10/1999 | | |
| WO | WO 99/51162 | 10/1999 | | A61D/17/32 |
| WO | WO 99/62430 | 12/1999 | | A61F/2/06 |
| WO | WO 00/09195 | 2/2000 | | A61M/29/00 |
| WO | WO 00/24449 | 5/2000 | | A61M/25/00 |
| WO | WO 00/56387 | 9/2000 | | A61M/25/00 |
| WO | WO 01 49187 | 7/2001 | | A61B/17/11 |
| WO | WO 01/60427 | 8/2001 | | |

OTHER PUBLICATIONS

Bernhard Meier, "Total Coronary Occlusion: A Different Animal?", Journal of the American College of Cardiology, vol. 17, No. 6, May 1991; pp. 50B–57B.

Puma, J. et al., "Percutaneous Revascularization of Chronic Coronary Occlusions: An Overview", JACC, vol. 26, No. 1, Jul. 1995, pp. 1–11.

Werner, G. et al., "Vessel Reconstruction in Total Coronary Occlusions With a Long Subintimal Wire Pathway: Use of Multiple Stents Under Guidance of Intravascular Ultrasound", Catheterization and Cardiovascular Diagnosis, vol. 40, pp. 46–51, (1997).

Sirnes, P. et al., "Stenting in Chronic Coronary Occlusion (SICCO): A Randomized, Controlled Trial of Adding Stent Implantation After Successful Angioplasty", JACC, vol. 28, No. 6, Nov. 15, 1996, pp. 1444–1451.

* cited by examiner

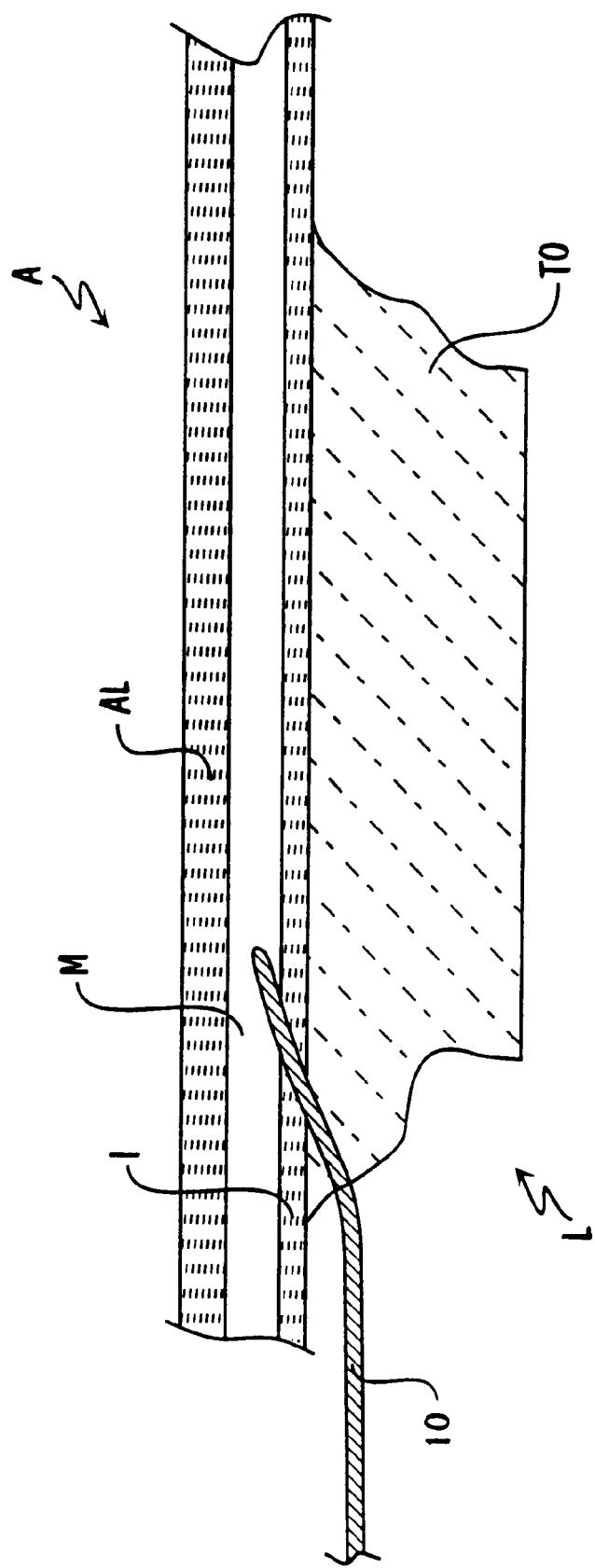

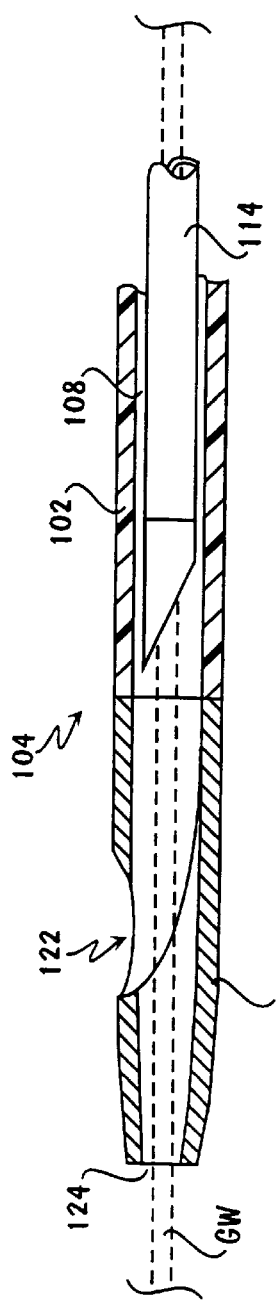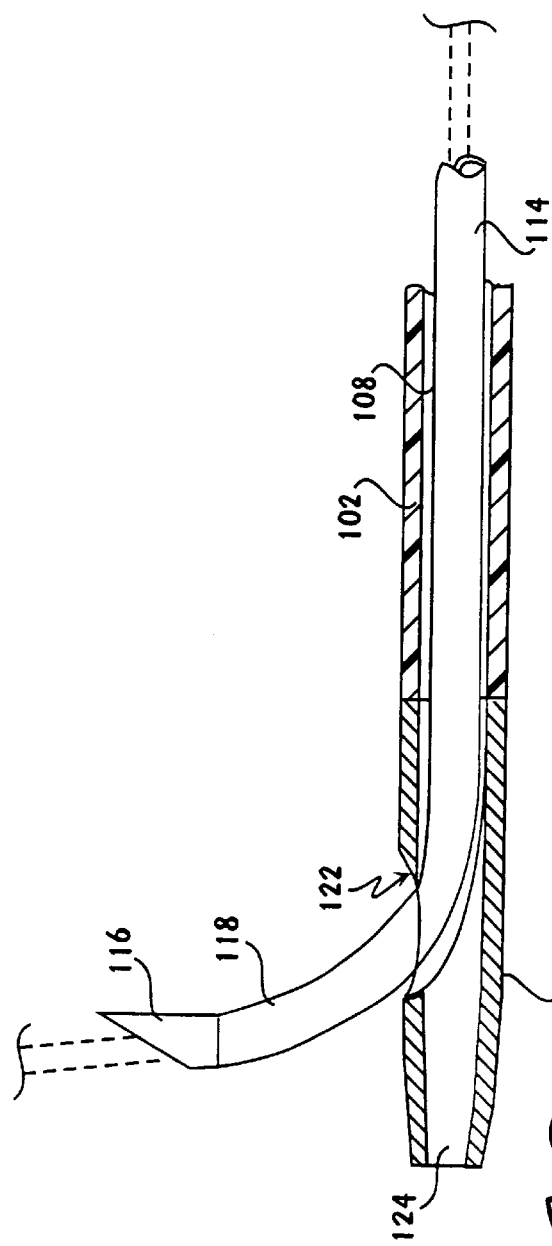

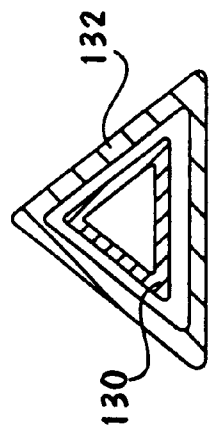
FIG. IIB
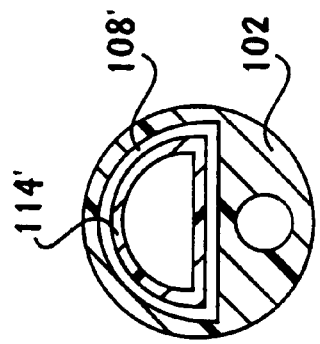
FIG. 12
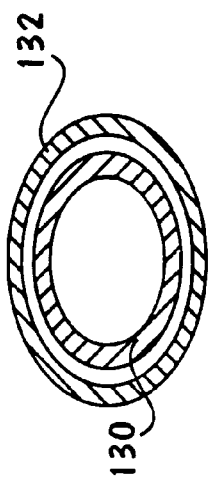
FIG. IIA

VASCULAR RE-ENTRY CATHETER

RELATED APPLICATIONS

This is a continuation of U.S. Pat. No. 6,235,000, filed Nov. 17, 1999, which is a division of U.S. Pat. No. 6,231,546, filed Jan. 13, 1998.

BACKGROUND OF THE INVENTION

1. Field of the Invention

The present invention relates generally to medical devices, kits, and methods. More particularly, the present invention relates to systems and procedures for crossing chronic total occlusions in blood vessels with guidewires and subsequently performing angioplasty, atherectomy, stenting, or other treatments.

Cardiovascular disease is a leading cause of mortality worldwide. Cardiovascular disease can take many forms, and a variety of specific interventional and pharmaceutical treatments have been devised over the years with varying levels of success.

A particularly troublesome form of cardiovascular disease results when a blood vessel becomes totally occluded with atheroma or plaque, referred to as a chronic total occlusion. Until recently, chronic total occlusions have usually been treated by performing a bypass procedure where an autologous or synthetic blood vessel is anastomotically attached to locations on the blood vessel upstream and downstream of the occlusion. While highly effective, such bypass procedures are quite traumatic to the patient.

Recently, catheter-based intravascular procedures have been utilized to treat chronic total occlusions with increasing success. Catheter-based intravascular procedures include angioplasty, atherectomy, stenting, and the like, and are often preferred because they are much less traumatic to the patient. Before such catheter-based treatments can be performed, however, it is usually necessary to cross the occlusion with a guidewire to provide access for the interventional catheter. In some instances, crossing the occlusion with a guidewire can be accomplished simply by pushing the guidewire through the occlusion. The guidewire remains in the blood vessel lumen and provides the desired access path. In many cases, however, the guidewire inadvertently penetrates into the subintimal space between the intimal layer and the adventitial layer of the blood vessel as it attempts to cross the occlusion. Once in the subintimal space, it is very difficult and in many cases impossible to direct the guidewire back into the blood vessel lumen. In such cases, it will usually be impossible to perform the catheter-based intervention and other, more traumatic, procedures may have to be employed.

For these reasons, it would be desirable to provide methods, kits, and apparatus which facilitate crossing a chronic total occlusion in a blood vessel with a guidewire. In particular, it would be desirable to provide catheters, guides, or other apparatus which could be used with a conventional or specialized guidewire to direct or redirect the guidewire from the subintimal space back into the blood vessel lumen after the guidewire has entered such space. Such methods and apparatus should be useful in coronary arteries as well as other blood vessels and should be capable of being performed with or without imaging from within or adjacent to the blood vessel. The apparatus for achieving these objective should be of simple construction and be capable of being used in a straight-forward, generally foolproof manner. At least some of these objectives will be met by the invention described hereinafter.

2. Description of the Background Art

Catheters having side guidewire entry ports spaced proximally from their distal tips are described in U.S. Pat. Nos. 5,464,395; 5,413,581; 5,190,528; 5,183,470; 4,947,864; and 4,405,314. Catheters and methods for forming lateral penetrations through tissue to and from blood vessels past total occlusions are described in U.S. Pat. Nos. 5,443,497; 5,429,144; 5,409,019; 5,287,861; WO 97/13463; and WO 97/13471.

SUMMARY OF THE INVENTION

According to the present invention, methods are provided for crossing total occlusions in blood vessels. While the methods are particularly beneficial for the treatment of coronary artery disease, they are also useful in the treatment of other arteries and veins, such as the treatment of peripheral vascular diseases.

The total occlusions are crossed by first forming a track from a lumen in the blood vessel into a subintimal space between an intimal layer and an adventitial layer of the blood vessel. The track is formed so that it extends from a location proximal of the total occlusion to a location which is distal to the total occlusion. A passage is then formed from the track back into the blood vessel lumen at the distal location. In the specific embodiments, the track is formed by advancing a wire through the blood vessel lumen into the subintimal space, typically by advancing the wire until it encounters the total occlusion. By continuing to advance the wire, it will usually pass into the subintimal space and can be further advanced to the desired distal location. After the wire is located distally to the total occlusion, it is typically deflected from the track back into the blood vessel lumen.

In the exemplary methods, the wire is deflected using a deflecting catheter. Typically, the deflecting catheter is advanced over a proximal end of the wire and advanced into the track within the subintimal space. The wire and the deflecting catheter are then manipulated so that the wire is deflected laterally through the intimal layer back into the blood vessel lumen. Such deflecting catheters are also useful in supporting the wire as it is advanced into and/or through the track, i.e. the catheter can enhance the "pushability" of the wire when it is advanced forward through any resisting material. Specific designs for such deflecting catheters are described in detail below. Alternatively, the wire which is initially positioned within the track in the subintimal space may be withdrawn through the deflecting catheter and exchanged for a second wire or other device suitable for penetrating through the intimal layer back into the blood vessel lumen. It will be appreciated that the wires and/or deflecting and other catheters may be freely exchanged over or through one another in a conventional matter without departing from the present invention.

It will usually be necessary to determine when the wire and/or deflecting catheter are positioned distal to the total occlusion so that the wire may be returned to the blood vessel lumen beyond said occlusion. Most simply, such position determination can be made by fluoroscopically imaging the blood vessel in a conventional manner. Alternatively or additionally to such fluoroscopic imaging, intravascular imaging, e.g. intravascular ultrasonic imaging (IVUS), and a variety of optical imaging modelities, such as optical coherence tomography (OCT), may be employed. For example, an ultrasonic imaging guidewire may be used to initially access the subintimal space and/or may be exchanged for the wire which is used to access the subintimal space. An imaging guidewire present in the subintimal space may readily detect the presence or absence of occluding material within the blood vessel lumen. When the transition from occluding material to lack of occluding material is detected, it is known that the position of the guidewire has advanced beyond the total occlusion.

After the passage is formed back from the track into the blood vessel lumen and a wire is in place across the total occlusion, the wire is available for use as a guidewire in positioning interventional and diagnostic catheters across the total occlusion. Most commonly, interventional catheters will be positioned across the total occlusion for treating the occlusion. Exemplary interventional catheters include angioplasty balloon catheters, rotational atherectomy catheters, directional atherectomy catheters, stent-placement catheters, and the like.

In a preferred aspect of the methods of the present invention, the wire deflecting step will comprise deflecting a cannula from the subintimal space back into the blood vessel lumen and thereafter passing the wire through a path defined by the cannula, typically by a lumen within the cannula. Usually, the cannula will be advanced over the wire after the wire is disposed within the subintimal space, and the cannula-deflecting step will comprise advancing a resilient (pre-formed) curved end of the cannula from a constraining lumen into the blood vessel lumen. Alternatively, the wire-deflecting step may comprise advancing a deflecting catheter over the wire which has been advanced into the subintimal space. A cannula may then be advanced through a lateral opening of the deflecting catheter and penetrated through the intimal layer to define a path for the wire back into the blood vessel lumen. Steerable and other actively deployed cannulas may also be used.

The present invention further provides kits comprising a wire-deflecting catheter having a lumen or mechanism capable of laterally deflecting a wire. The kit will further comprise instructions setting forth any of the methods described above. Optionally, the kit may further comprise the wire which is used for penetrating the subintimal space and/or back into the blood vessel lumen. The kit will usually still further comprise a package for containing both the wire deflecting catheter and the instructions, and optionally the additional wire(s). Suitable packages include pouches, trays, tubes, boxes, and the like. The instructions may be printed on a separate package insert or may be printed in part or in whole on the packaging itself. Usually, the components of the kit within the package will be sterilized by conventional procedures.

Apparatus according to the present invention comprise wire-deflection systems. Exemplary wire-deflection systems usually comprise the wire-deflecting catheter which includes a catheter body and a deflecting cannula. The catheter body will have a proximal end, a distal end, and at least one lumen extending through at least a distal portion thereof. The lumen will have a distal opening and a lateral opening. The cannula also has a proximal end, a distal end, and at least one lumen extending through a distal portion thereof. The distal portion of the cannula will have a preformed, resilient curve. The cannula will be slidably disposed within the lumen of the catheter body to assume (a) a straightened configuration when the cannula is proximally retracted within the catheter body lumen and (b) a curved configuration when the cannula is extended laterally through the lateral opening of the catheter body. In this way, the cannula can be selectively deflected through the intimal layer of the blood vessel according to the preferred methods described above. The system may further comprise a wire configured to pass through the cannula lumen. The wire may be a conventional guidewire, but will more typically be a wire having a sharpened distal tip intended particularly for penetrating the intimal layer of the blood vessel wall. Optionally, the wire may further comprise an imaging means such as an ultrasonic imaging means. The catheter body will typically have a fluoroscopically visible marker near its distal end. The marker will be configured to permit visual determination of the rotational orientation of the distal end of the catheter body when viewed in a two-dimensional fluoroscopic image. The catheter body will usually be reinforced to enhance torsional rigidity, and may further comprise a distal nose cone wherein the distal and lateral openings are defined within the nose cone. The distal end of the cannula will usually be pre-formed in a smooth curve which may extend over an arc in the range from 15° C. to 135° C., usually from 45° C. to 90° C. The pre-formed curve may have a radius in the range from 0.5 mm to 15 mm, usually from 2 mm to 10 mm.

BRIEF DESCRIPTION OF THE DRAWINGS

FIGS. 3A-3D illustrate the method of the present invention for crossing a total occlusion with a wire using a deflecting catheter.

FIGS. 3BB illustrates an alternate guidewire advancement step for the method of FIGS. 3A-3D.

FIGS. 8 and 9 are detailed, cross-sectional views of the distal end of the catheter of FIG. 7, illustrating an internal cannula in a retracted and advanced configuration, respectively.

FIGS. 11A and 11B illustrate a configuration for rotationally keying the proximal end of the catheter of FIGS. 7-10.

FIG. 12 illustrates a configuration for rotationally keying the distal end of the catheter of FIGS. 7-10.

DESCRIPTION OF THE SPECIFIC EMBODIMENTS

Figure 1:
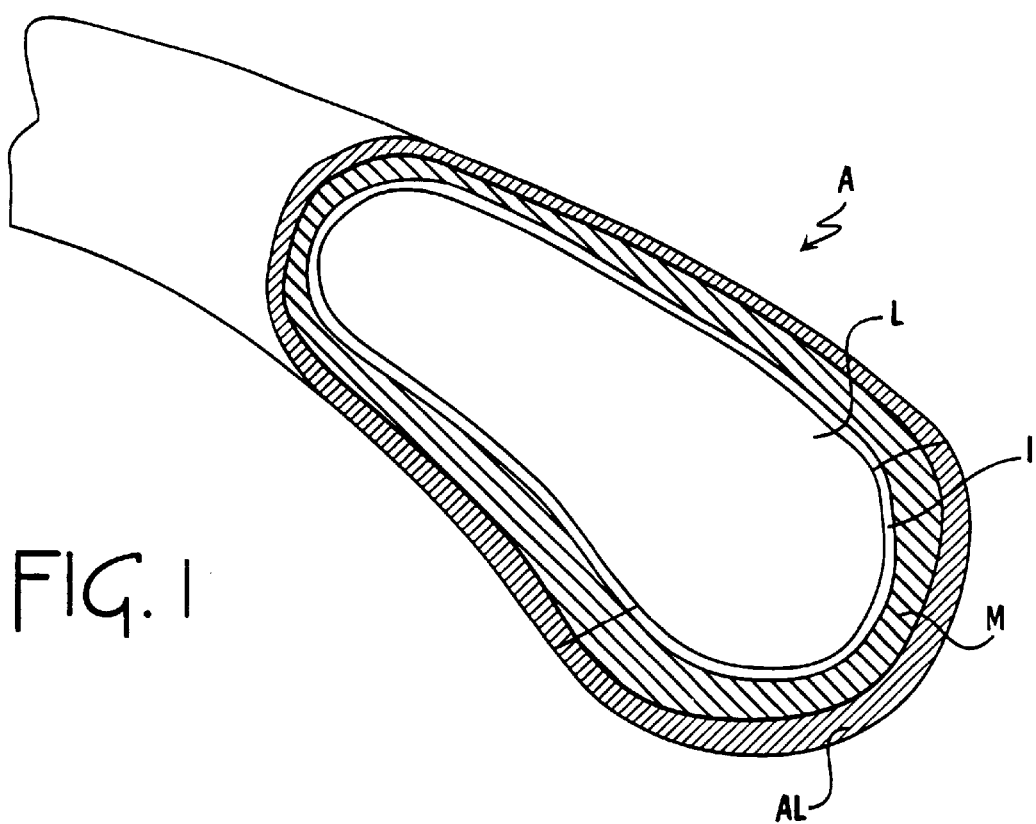
FIG. 1 is a schematic illustration of a coronary artery showing the intimal layer, the medial layer, and the adventitial layer.

Referring to FIG. 1, a normal (non-diseased) artery A comprises a lumen L and an arterial wallhaving a number of layers. The tissue of the arterial wass is collectively referred to herein as the extraluminal space within the artery or blood vessel. The innermost layer of the arterial wall is referred to herein as the intimal layer I which includes the endothelium, the sibendothelial layer, and the internal elastic lamina. A medial layer M is concentrically outward from the intimal layer, and an adventitial layer AL is the outermost layer. Beyond the adventitial layer AL lies the extravascular tissue.

As used hereinafter, the region beteween the intimal layer I and the adventitial layr AL, generally including the medial layer M, will be referred to as the subintimal space. It is the subintimal space through which the wires, deflecting catheters, and other catheter of the present invention will pass when crossing a total occlusion.

Figure 2:
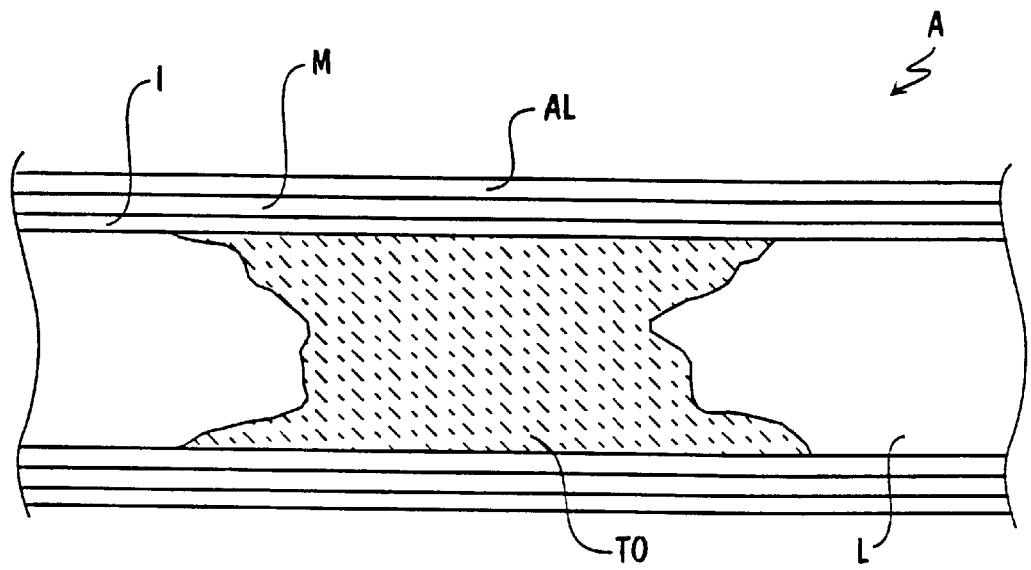
FIG. 2 is a schematic illustrations of a total occlusion within the coronary artery of FIG. 1, shown in full section.

Referring now to FIG. 2, a total occlusion TO within the artery A is illustrated. Total occlusion TO may comprise atheroma, plaque, thrombus, and/or other occluding materials normally associated with cardiovascular disease. By "total" occlusion, it is meant that the occluding material occludes substantially the entire lumen L of the artery or other blood vessel so that blood flow through the vessel is substantially stopped. The present invention will usually be used with patients where the totally occluded artery is not immediately life threatening since the tissue distal to the occlusion will receive oxygenated blood from collateral arteries. Usually, however, the blood supply will be insufficient and it will be desirable to treat the occlusion by an intravascular intervention, such as angioplasty, atherectomy, stenting, or the like, to restore blood flow through the affected vessel.

Figure 3B:
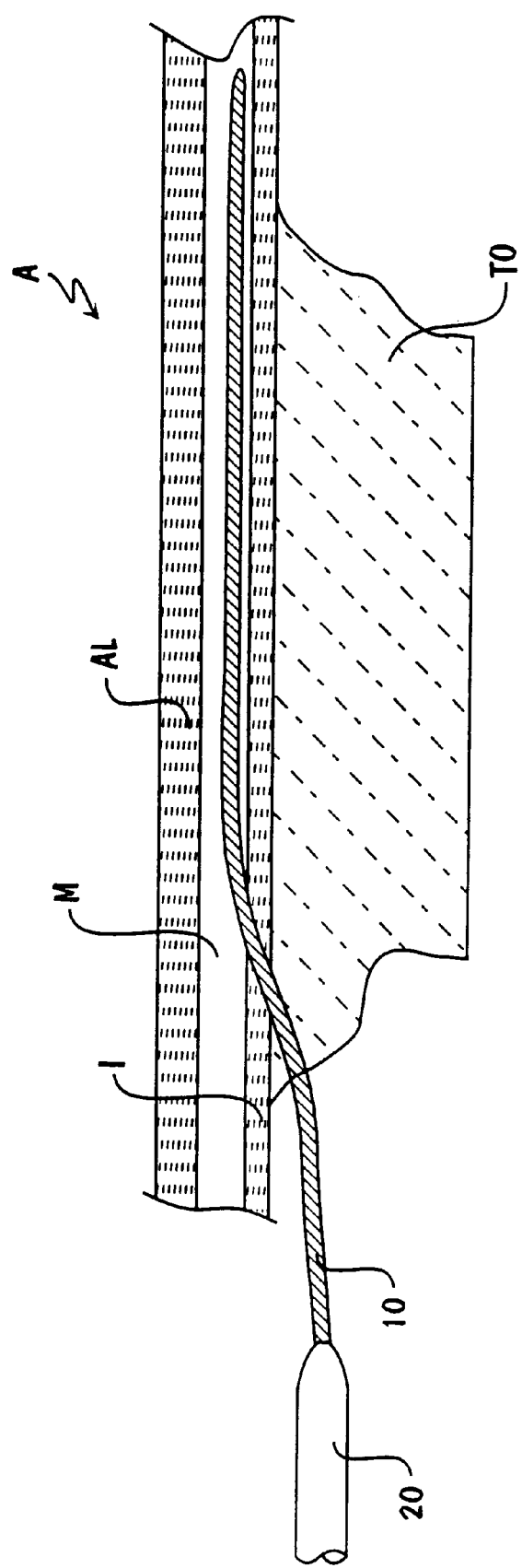
Figure 3B:
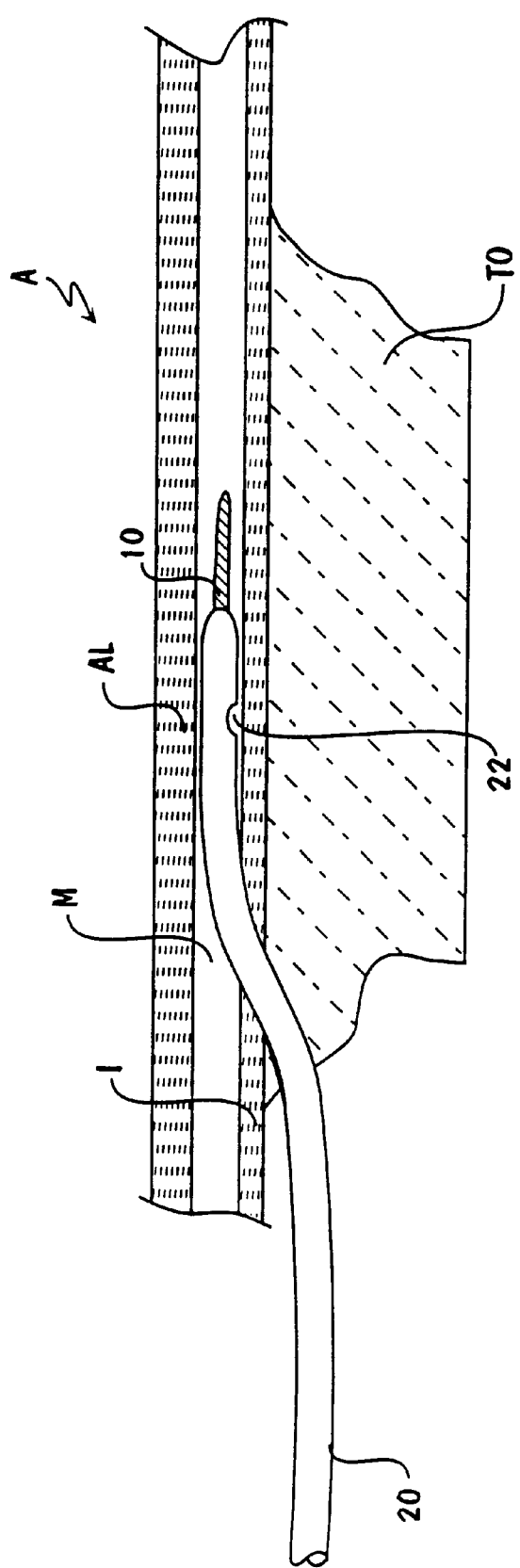

The method of the present invention will be described with reference to FIGS. 3A–3D. These figures represent an upper portion of the artery of FIG. 2. As seen in FIG. 3A, a wire 10 is advanced through the lumen of the artery until it encounters the total occlusion TO. At that time, it is possible that the wire 10 will advance through the occlusion without deflecting into the blood vessel wall. Should that occur, subsequent repositioning of the guidewire according to the methods of the present invention may not be necessary. More usually, however, the wire 10 will advance into the subintimal space within the medial layer M, as shown in FIG. 3A. The intimal layer I and adventitial layer AL together define a "tissue plane" through which the wire will naturally pass as the wire is pushed distally from its proximal end. The wire 10 will continue to advance until its tip passes beyond the distal end of the total occlusion TO, as shown in FIG. 3B. The tip could axially advance well beyond the total occlusion until advancement is ceased.

FIG. 3B shows the guidewire 10 advancing without support. In some instances, however, the guidewire 10 may encounter significant resistance as it enters and/or passes through the space between the intimal layer T and adventitial layer AL. If resistance is encountered, the deflection, catheter 20 may be used to support and enhance the "pushability" of the guidewire 10 by advancing the catheter to a location just proximal of the distal tip of the guidewire, as shown in FIG. 3B. The guidewire 10 and catheter 20 may then be advanced sequentially, e.g. advancing the guidewire a short distance followed by advancing the catheter, and so on.

Figure 3C:
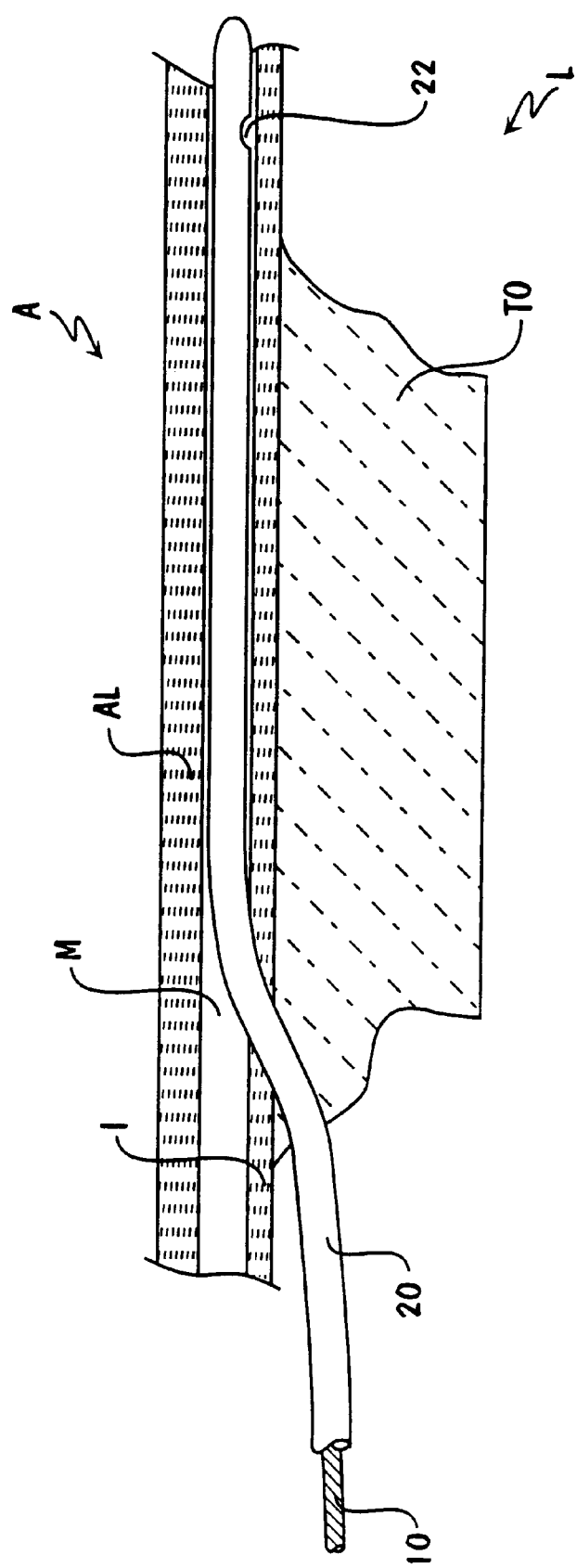
Figure 3D:
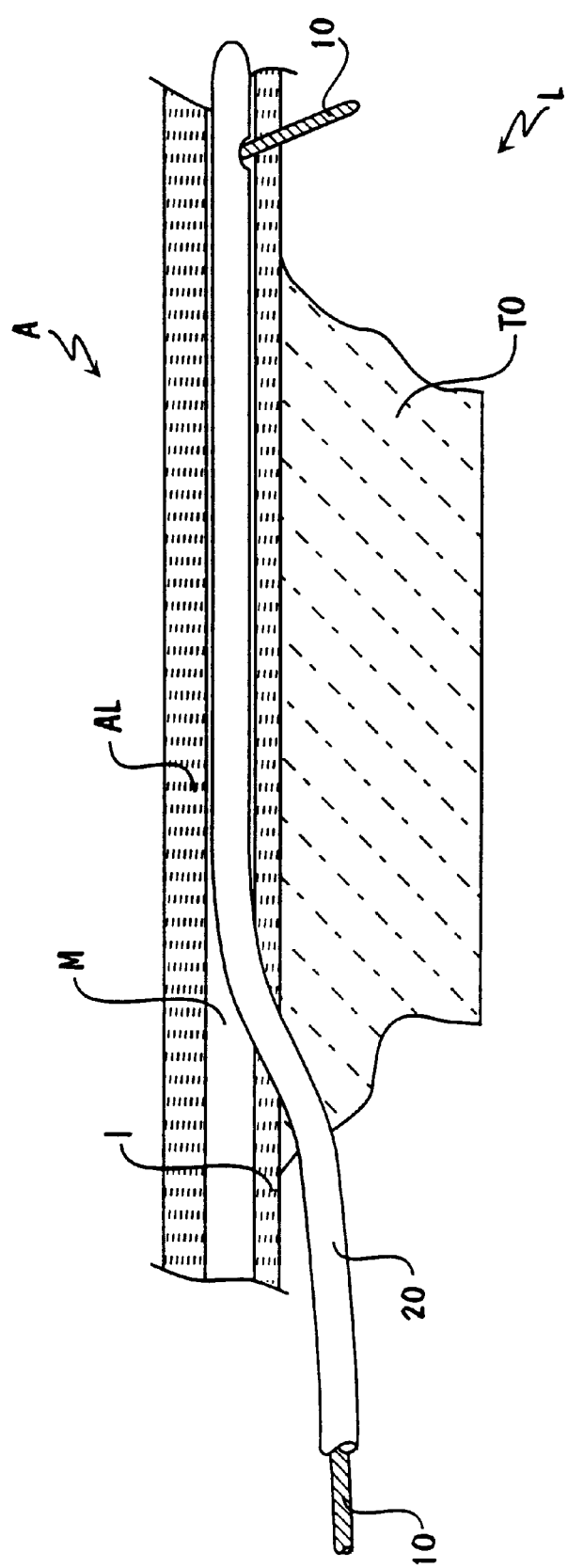

According to the present invention, however, once the wire 10 has its distal tip positioned beyond the total occlusion TO, deflecting catheter 20 may be advanced over the wire 10, by coaxial introduction over the proximal end of the wire, until it approaches the total occlusion, also as shown in FIG. 3B. The deflecting catheter 20 is then further advanced over the wire 10 until its distal tip also extends beyond the total occlusion TO, as illustrated in FIG. 3C. The deflecting catheter 20 will include some mechanism for laterally deflecting the wire 10 so that it may pass back in a radially inward direction through the intimal layer I back into the blood vessel lumen L. The deflection mechanism may take a variety of forms as described below. As shown in FIG. 3C, a lateral port 22 is provided. The wire 10 may be retracted so that its distal tip lies proximally of the port 22 and then advanced distally so that the wire passes laterally outwardly through the port and back into the blood vessel lumen, as shown in FIG. 3D.

In order to optimize performance of this method, it is usually desirable to assure that the distal tip of the wire 10 and the deflecting port 22 (or other deflecting mechanism) of the deflecting catheter 20 are properly positioned beyond the total occlusion TO without being advanced excessively beyond the end of the total occlusion. Typically, it will be desirable to position the deflecting mechanism at from 0 cm to 2 cm beyond the distal end of the total occlusion TO, preferably from 0 cm to 0.5 cm. As discussed above, such positioning can in some instances be performed using conventional fluoroscopic imaging. For example, in some instances it may be sufficient to provide suitable radiopaque markers on the wire and on the deflecting mechanism of the deflecting catheter 20 permitting visual positioning of the tip via fluoroscopy. Often, however, it will be desirable to provide ultrasonic or other imaging at or near the total occlusion. In one approach, wire 10 may be provided with ultrasonic imaging so that the presence and absence of the occluding material may be detected as the wire is advanced passed the total occlusion TO. Alternatively, the deflecting catheter 20 may be provided with such ultrasonic imaging, e.g. in the form of a phased array located near the distal tip (not shown). Ultrasonic imaging guidewires are described in the patent literature. See, e.g. U.S. Pat. No. 5,095,911, the full disclosure of which is incorporated herein by reference. As yet another alternative, an imaging guidewire may be advanced to the region of the total occlusion TO in a direction opposite to that of the wire 10 and catheter 20. In this way, the imaging guidewire need not advance through the total occlusion, but could still detect advancement of the catheter and/or guidewire, particularly if ultrasonically opaque components were provided on either or both of the catheter and wire. In yet another alternative, an ultrasonic imaging catheter or guidewire could be positioned in a vein adjacent to the arterial occlusion site, allowing imaging of the entire occluded region while the guidewire is advanced there through. Other imaging modalities, such as optical coherence tomography (OCT) (see U.S. Patent Nos. 5,321, 501; 5,459,570; 5,383,467; and 5,439,000) fluorescence imaging (see U.S. Pat. Nos. 4,718,417; and 5,106,387) and Raman spectroscopy (WO 92/18008), may also be employed.

A second desirable feature of the method of the present invention will be rotational positioning of the deflecting catheter 20. It will be appreciated that the direction of deflection is usually selective, and therefore it will be desirable to aim the deflecting mechanism from the subintimal space back toward the arterial or other blood vessel lumen L. If the catheter 22 is provided with ultrasonic imaging, such imaging can be used for rotationally positioning the distal tip of the catheter. The catheter will be rotationally rigid so that rotation of its proximal end. may position the distal end. By then detecting the presence of the blood vessel lumen, the deflecting port 22 or other deflecting mechanism can be properly positioned. In an alternative embodiment, as illustrated below in connection with the exemplary catheter, a rotationally specific fluoroscopic marker may be provided on the catheter 20. The marker will be such that by observing the two-dimensional image of the marker by fluoroscopic imaging, the rotational direction of the catheter tip can be determined.

Figure 4:
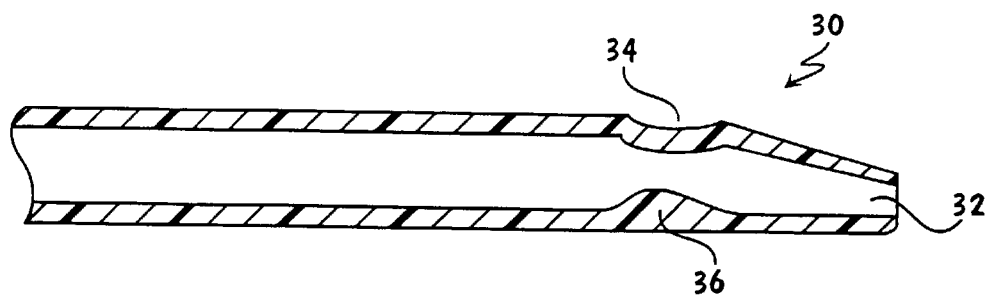
FIG. 4 illustrates a first embodiment of the distal end of a deflecting catheter suitable for use in the methods of the present invention.
Figure 5:
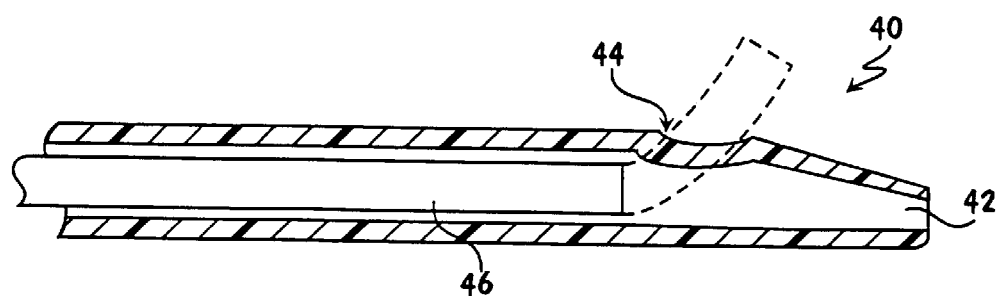
FIG. 5 illustrates a second embodiment of the distal end of a deflecting catheter useful in the methods of the present invention.
Figure 6:
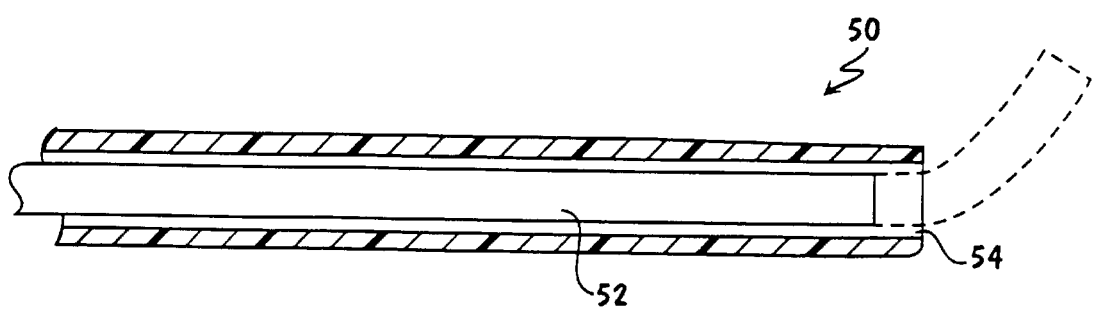
FIG. 6 illustrates a third embodiment of the distal end of a deflecting catheter useful in the methods of the present invention.

Referring now to FIGS. 4–6, exemplary deflecting mechanisms for the deflecting catheters of the present invention will be described. In FIG. 4, the distal end of the catheter 30 has a distal port 32, a lateral port 34, and a passive deflecting mechanism 36. The catheter 30 may be advanced over the proximal end of a wire so that the wire passes over the deflecting mechanism 36 and back into the main lumen of the catheter 30. The catheter 30 may then be advanced over the wire until the distal tip enters the subintimal space and approaches the distal end of the wire. By retracting the distal end of the wire within the lumen of catheter 30 so that its distal tip is proximal to the deflecting mechanism 36, subsequent distal advancement of the wire will engage the proximal surface of the deflecting mechanism and cause the wire to be deflected laterally through lateral port 34.

A first active deflecting mechanism is illustrated in FIG. 5. There, catheter 40 has a distal port 42 and a lateral port 44. Rather than a passive deflecting mechanism, catheter 40 includes an axially translatable cannula 46 having a resilient, pre-formed distal tip which may be advanced through port 44, as shown in broken line. The cannula 46 has a lumen which provides a guide path for the wire.

Catheter 50 illustrated in FIG. 6 is similar to catheter 40 in FIG. 5, except that no lateral port is provided. Instead, a cannula 52 having a pre-formed distal end may be advanced and retracted out of a distal port 54 of the catheter 50 so that its distal end can assume a laterally deflected shape, as shown in broken line. It will be appreciated that these three embodiments are intended to be exemplary only. A wide variety of other passive and active deflecting mechanisms could be provided on deflecting catheters for use in the methods of the present invention.

Figure 7:
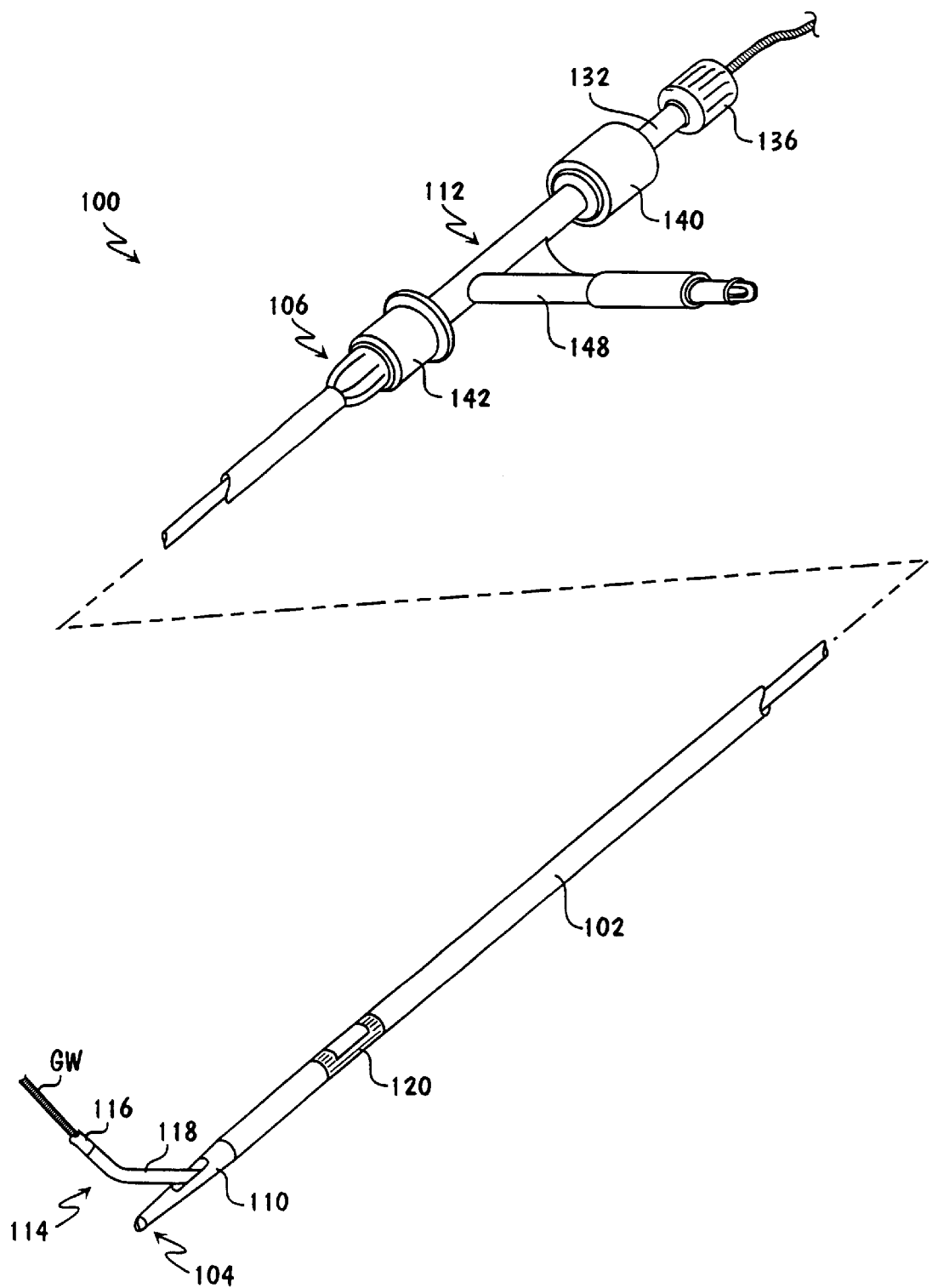
FIG. 7 illustrates a presently preferred embodiment for the wire-deflecting catheter and system of the present invention.

Referring now to FIGS. 7–10, a presently preferred exemplary deflecting catheter 100 constructed in accordance with the principles of the present invention will be described. The deflecting catheter 100 comprises a catheter body 102 having a distal end 104 and a proximal end 106. Catheter body 102 includes a single lumen 108 (FIGS. 8 and 9), and a deflecting housing 110 secured to the distal end 104 thereof. An actuator hub 112 is secured to the proximal end 106 of catheter body 102, and an axially translatable cannula is disposed within lumen 108. The cannula 114 has a sharpened tip 116, typically formed from a metal, hard plastic, composite, or the like, optically being radiopaque. Alternatively or additionally, it may be desirable to provide at least one separate radiopaque marker or the cannula at or near its distal end to facilitate visualization under fluoroscopic imaging. A distal length 118 of the cannula 114 is pre-formed in a curved shaped, as best seen in FIGS. 7 and 9. A rotationally specific radiopaque marker 120 is mounted near the distal end of catheter body 102. As illustrated, the marker has a generally U-shaped configuration so that the rotational position of the distal end of the catheter body 102 will be apparent when the marker is observed in a two-dimensional fluoroscopic image.

As with catheter 40 in FIG. 5, the purpose of catheter 100 is to laterally deflect the distal tip of the cannula 114 through a lateral opening 122 in the deflector housing 110. The deflector housing 110 also includes a distal port 124 to permit introduction of the catheter 100 over the proximal end of a guidewire GW, as illustrated in FIG. 8 in broken line. The guidewire GW will pass through the distal port 124 and into the distal end of the cannula 114 and travel through a lumen of cannula 114 all the way to the proximal end of the catheter 100. The distal length 118 of cannula 114 will be straightened and deflected by axially retracting and advancing the cannula between the configuration shown in FIG. 8 and FIG. 9, respectively.

Figure 10:
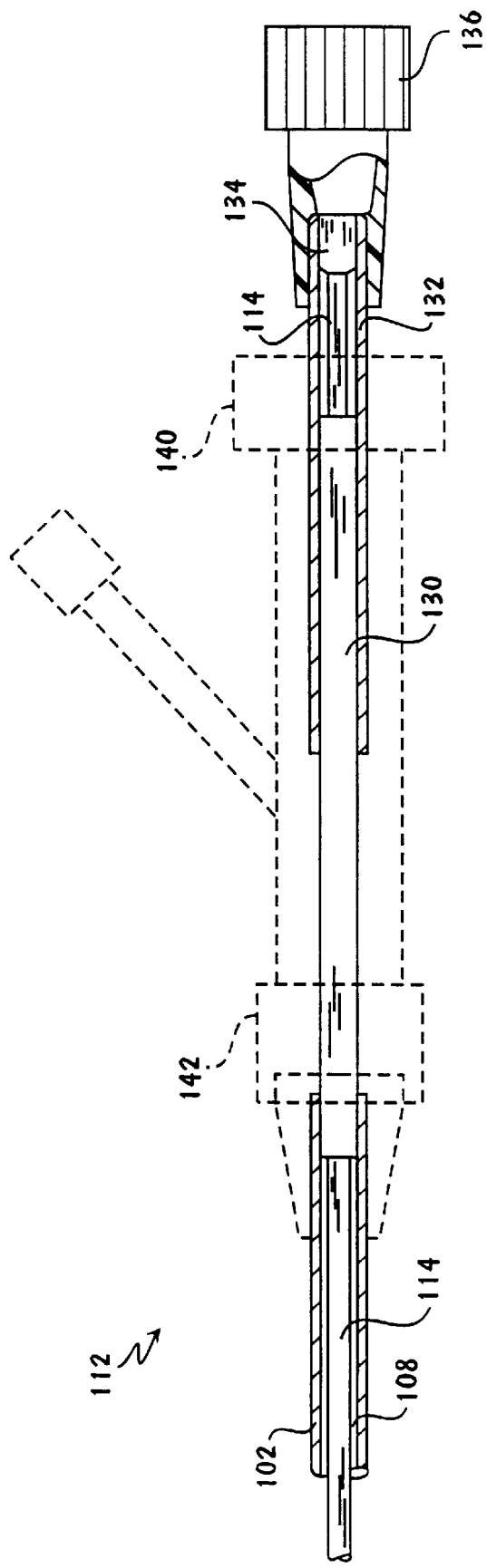
FIG. 10 is a schematic illustration of a proximal hub of the catheter of FIG. 7.

Referring now to FIG. 10, the actuator hub 112 comprises a pair of coaxial, telescoping tubes 130 and 132. The outer telescoping tube 132 is connected to a proximal end of cannula 114, typically by an adhesive 134. A proximal fitting 136 is further attached to the proximal end of tube 132 so that the assembly of the cannula 114, tube 132, and fitting 136 will move together as a unit through the hemostatic fitting 140 at the proximal end of the hub 112. Hub 112 further includes a rotational fitting 142 which permits the catheter body 102 to be rotated relative to the is hub body. The cannula 114 and catheter body 102 will be rotationally coupled or "keyed" together to limit or prevent relative rotation, typically by keying within the hub and/or near the distal end, so that rotation of the catheter body causes a like rotation of the cannula as the catheter is rotationally positioned within a blood vessel. A side branch 148 is provided on hub 112 to permit perfusion and/or infusion through the lumen 108 of catheter 102.

Keying at the proximal end of the catheter 100 can be achieved in a variety of ways. For example, the telescoping tubes 130 and 132 can be provided with asymmetric, mating peripheral geometries, such as oval cross-sections (FIG. 11A) or triangular cross-sections (FIG. 11B). Keying at the distal end can also be achieved in a number of ways, such as providing the catheter body 102 with an asymmetric lumen 108 and the cannula 114 with a mating cross-section, e.g. a D-shaped cross-section as illustrated in FIG. 12. The ability to limit relative rotation of the cannula 114 within the catheter body 102 is advantageous since it assures that curved distal length 118 is properly oriented (usually directed radially outwardly) when the tip 116 emerges through the opening 122.

In use, catheter 100 will be advanced over guidewire GW while the cannula 114 is retracted, as shown in FIG. 8.

Once the catheter is properly positioned, cannula 114 may be distally advanced, as shown in FIG. 9. Distal advancement is achieved by forwardly advancing the sleeve 132 in hub 136 relative to the remainder of the hub 112 so that the cannulas move forwardly within the lumen 108 of catheter body 102. Prior to advancing the cannula, the port 122 will be properly positioned so that it is directed toward the blood vessel lumen by rotating catheter body 102, typically using the rotational hub 142. Conveniently, the physician will observe the marker 120 so that the lateral port 122 will be directed in the proper radially inward direction. After the cannula has been advanced into the blood vessel, the guidewire GW may then be advanced into the lumen, the cannula 114 withdrawn proximally, and the entire catheter assembly then withdrawn from over the guidewire, leaving the guidewire in place for introduction of other interventional and/or diagnostic catheters.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for forming a pathway between an extraluminal space within a blood vessel and a lumen of the blood vessel, comprising:

advancing a wire into the extraluminal space of a wall of the blood vessel;

advancing a catheter system over the wire into the extraluminal space;

retracting the wire into the catheter system; and advancing the wire through a lateral port in the catheter system, wherein the pathway is formed from the extraluminal space into the lumen.

2. The method of claim 1, wherein advancing comprises deflecting.

3. A method for forming a pathway between an extraluminal space within a blood vessel and a lumen of the blood vessel, comprising:
- advancing a wire into the extraluminal space of a wall of the blood vessel;
- advancing a catheter system into the extraluminal space;
- positioning the wire in the catheter system; and
- advancing the wire through a lateral port in the catheter system, wherein the pathway is formed from the extraluminal space into the lumen.

4. A method for forming a pathway between an extraluminal space within a blood vessel and a lumen of the blood vessel, comprising:
- advancing a catheter system into the extraluminal space of a wall of the blood vessel;
- positioning a wire in the catheter system;
- positioning a port of the catheter system towards the lumen using a visualization subsystem of the catheter system; and
- advancing the wire through the port to form the pathway from the extraluminal space into the lumen.

5. The method of claim 4, wherein the visualization subsystem includes at least one system selected from among ultrasound system, an intravascular ultrasonic imaging system (IVUS), an optical coherence tomography (OCT) system, and a fluoroscopic system.

6. The method of claim 4, wherein the wire includes the visualization subsystem.

7. A method for forming a pathway between an extraluminal space within a blood vessel and a lumen of the blood vessel, comprising:
- advancing a catheter system into the extraluminal space of a wall of the blood vessel;
- positioning a working element in the catheter system;
- positioning a port of the catheter system towards the lumen using a visualization subsystem of the catheter system; and
- advancing the working element through the port to form the pathway from the extraluminal space into the lumen.

8. The method of claim 7, further comprising advancing a guide wire into the extraluminal space, wherein advancing the catheter system includes tracking the catheter system over the guide wire to a target location.

9. The method of claim 7, wherein the working element is a cannula.

10. The method of claim 7, wherein the working element is a cannula having a pre-shaped distal tip.

11. The method of claim 7, wherein die working element is a needle cannula having a pre-shaped distal tip.

12. A method for forming a pathway between an extraluminal space within a blood vessel and a lumen of the blood vessel, comprising:
- advancing a catheter system into the extraluminal space of a wall of the blood vessel;
- positioning a wire in the catheter system, wherein the wire includes a visualization subsystem;
- positioning a port of the catheter system towards the lumen using a visualization subsystem; and
- advancing the wire through the port to form the pathway from the extraluminal space into the lumen.

* * * * *

UNITED STATES PATENT AND TRADEMARK OFFICE
CERTIFICATE OF CORRECTION

PATENT NO.    : 6,511,458 B2
DATED         : January 28, 2003
INVENTOR(S)   : Charles F. Milo et al.

It is certified that error appears in the above-identified patent and that said Letters Patent is hereby corrected as shown below:

Column 10,
Line 19, cancel "die", and insert -- the --.
Line 29, cancel "using a visualization", and insert -- using the visualization --.

Signed and Sealed this

Eighteenth Day of March, 2003

JAMES E. ROGAN
*Director of the United States Patent and Trademark Office*